United States Patent [19]
Chikama

[11] Patent Number: 5,159,919
[45] Date of Patent: Nov. 3, 1992

[54] ENDOSCOPE COVER
[75] Inventor: Toshio Chikama, Tokyo, Japan
[73] Assignee: Machida Endoscope Co., Ltd., Tokyo, Japan
[21] Appl. No.: 648,196
[22] Filed: Jan. 31, 1991
[30] Foreign Application Priority Data
  Feb. 1, 1990 [JP] Japan .................. 2-008123
[51] Int. Cl.⁵ .................................. A61B 1/00
[52] U.S. Cl. ........................ 128/4; 604/171; 604/263
[58] Field of Search ............... 128/4, 6; 604/171, 263

[56] References Cited
U.S. PATENT DOCUMENTS

| | | | |
|---|---|---|---|
| 4,646,722 | 3/1987 | Silverstein et al. | 128/4 |
| 4,721,097 | 1/1988 | D'Amelio | 128/4 |
| 4,741,326 | 5/1988 | Sidau et al. | 128/4 |
| 4,869,238 | 9/1989 | Opie et al. | 128/6 |
| 4,878,485 | 11/1989 | Adair | 604/263 |
| 4,881,810 | 11/1989 | Hasegawa | 128/4 |
| 4,974,580 | 12/1990 | Anapliotis | 128/4 |
| 4,991,564 | 2/1991 | Takahashi et al. | 128/4 |
| 5,000,533 | 3/1991 | Gerwers | 350/96.2 |

FOREIGN PATENT DOCUMENTS
3909290 10/1989 Fed. Rep. of Germany ......... 128/4

Primary Examiner—Stephen C. Pellegrino
Assistant Examiner—Ralph A. Lewis
Attorney, Agent, or Firm—Levisohn, Lerner & Berger

[57] ABSTRACT

An endoscope cover comprising a cylindrical end rigid cover portion composed a flexible material, which is fitted to an endoscope to cover a distal end rigid portion of the endoscope. A transparent window arranged on a closed face formed on the distal end of the rigid cover to confront at least an observation port and an illuminating port, which are arranged on the distal end of the endoscope, and a bag-shaped covering member having a length covering at least an intermediate conduit portion of the endoscope, which is attached to the rear part of the endoscope. A groove or notched face is formed in the longitudinal direction of the outer periphery of the distal end rigid portion of the endoscope and an anchoring groove is formed on the circumferential face portion. Anchoring projections are formed at confronting positions on the inner circumferential face of the rigid cover and are fitted in the anchoring groove formed in the distal end rigid portion to attach the rigid cover to the top end rigid portion. The covering member is bonded to all or a part of the periphery of the intermediate conduit portion by using an adhesive.

9 Claims, 2 Drawing Sheets

ENDOSCOPE COVER

BACKGROUND OF THE INVENTION

The present device relates to a cover for covering the outer periphery of an endoscope when the endoscope is used.

After an endoscope is used in the body cavity of a patient, the endoscope is generally washed and disinfected. However, this washing and disinfecting operation requires much time and labor, and the working efficiency of the endoscope is very low. Furthermore, if this washing and disinfecting operation is not sufficiently performed, no satisfactory washing and disinfecting effect can be attained.

Accordingly, an idea of a disposable cover for covering the outer periphery of an endoscope when the endoscope is used has recently been proposed, and an example of the disposable cover is disclosed in Japanese Unexamined Patent Publication No. 61-179128.

The disclosed technique concerns an endoscope cover comprising a soft cylindrical covering member composed of a rubber or synthetic resin, which is attached to a rigid cover portion fitted to cover a distal end rigid portion of the endoscope.

According to this endoscope cover, the rigid cover is fitted to the distal end rigid portion of the endoscope, a flexible tube of the endoscope is entirely covered with the covering member from the top end side of the flexible tube, the endoscope is inserted in this state into the body cavity of a patient, and after the endoscope is used, the endoscope cover is dismounted and thrown away. When the endoscope is used again, the endoscope is covered with a new endoscope cover and is used in the above-mentioned manner. According to this technique, the endoscope need not be washed and disinfected, and a high sanitary effect is attained and the endoscope can be continuously used.

When the above-mentioned endoscope is inserted into the body cavity for the use, or is bent in the body cavity or repeatedly moved to and fro in the inserting direction, the rigid cover comes off from the distal end rigid portion or the covering member gets out of position. Even if the rigid cover does not come off, the field of vision is disturbed by slippage of the rigid cover.

Furthermore, if the rigid cover is tightly fitted, it is difficult to dismount the rigid cover. For example, if the rigid cover is screwed, the screw should be turned in the reverse direction when the rigid cover is dismounted, and this operation should be performed with both hands. Accordingly, the operation efficiency is low, and since both hands are used for the dismounting operation, the dirty endoscope should be put at a certain place and the problem of contamination arises.

It is a primary object of the present invention to protect the intermediate conduit portion of the endoscope from contamination during use, and to permit immediate reuse of the endoscope.

Another object of the present invention is to provide an endoscope cover, in which, the rigid cover is prevented from being taken off or getting out of position, and there can be attained an effect of ensuring complete covering.

Still another object of the present invention is to provide an endoscope cover, which can be taken off from the endoscope by one touch, and the removal of the used endoscope cover can be accomplished without contamination of the endoscope.

SUMMARY OF THE INVENTION

In accordance with the present device, the foregoing problems are solved by an endoscope cover comprising a cylindrical rigid cover composed of an flexible material, which is fitted to an endoscope to cover a distal end rigid portion of the endoscope, a transparent window arranged on a closed face formed on the distal end of the rigid cover to confront at least an observation port and an illuminating port, which are arranged on the distal end of the endoscope, and a bag-shaped covering member having a length covering at least an intermediate conduit portion of the endoscope, which is attached to the rear part of the endoscope, wherein a groove or notched face is formed in the longitudinal direction of the outer periphery of the distal end rigid portion of the endoscope and an anchoring groove is formed on the circumferential face portion, anchoring projections are formed at confronting positions on the inner circumferential face of the rigid cover and are fitted in the anchoring groove formed in the distal end rigid portion to attack the rigid cover to the distal end rigid portion, and the covering member is bonded to all or a part of the periphery of the intermediate conduit portion by using an adhesive.

In the above-mentioned structure, if the rigid cover is fitted to cover the distal end rigid portion of the endoscope, headed by the covering member, the anchoring projections are anchored in the groove formed in the distal end rigid portion by one touch and the transparent window is positioned and fixed to confront the observation port and illuminating port.

The covering member is extended along the intermediate conduit portion from the end and bonded to all or a part of the intermediate conduit portion by using an adhesive to cover the intermediate conduit portion entirely. In this state, the intermediate conduit portion can be inserted into the body cavity and used for the observation. After the use, the place separate from the anchoring projections is depressed, whereby the anchoring projections are taken off from the anchoring groove, and therefore, the rigid cover can be removed from the distal end rigid portion. Moreover, by injecting air under pressure within the covering member, the covering member is peeled from the intermediate conduit portion, and by drawing out the intermediate conduit portion from the covering member, the intermediate conduit portion can be taken out from the covering member without contamination. A new endoscope cover is then fitted to the endoscope, the endoscope and can be directly used again.

DETAILED DESCRIPTION OF THE PREFERRED EMBODIMENTS

An example of the present device will now be described with reference to the accompanying drawings.

Figure 1:
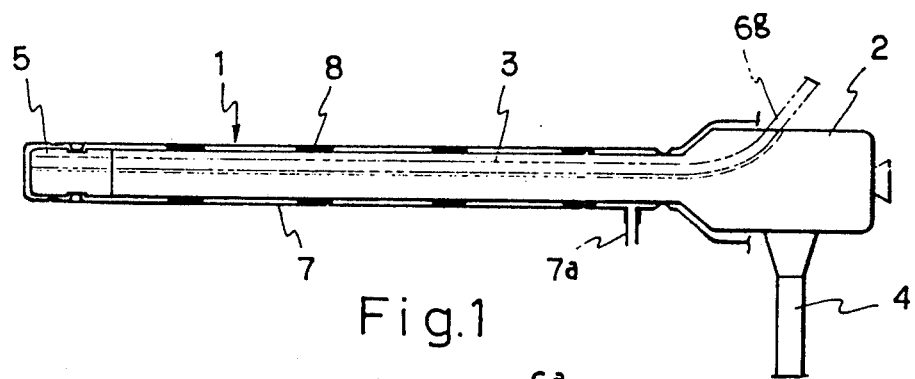
FIG. 1 is a side view illustrating the state where an endoscope cover is attached to an endoscope.
Figure 2:
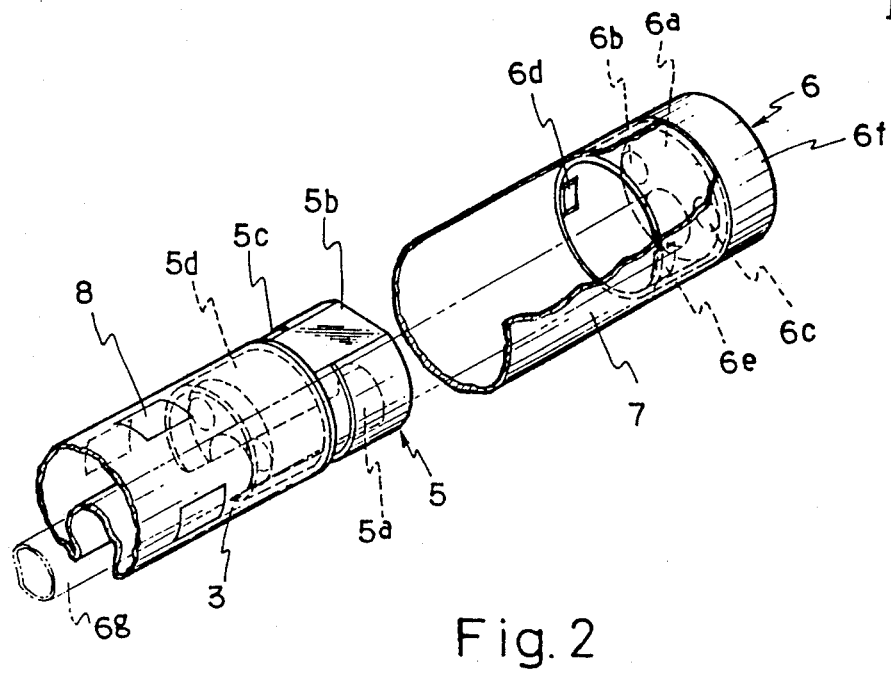
FIG. 2 is a perspective view illustrating the state of a distal end rigid portion and a rigid cover in the endoscope.
Figure 3:
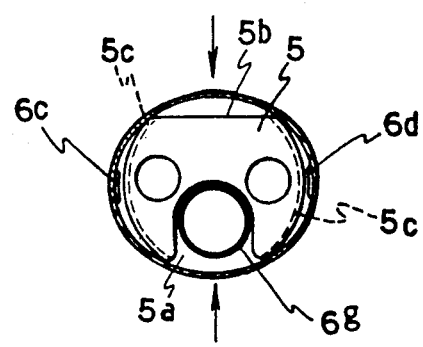
FIG. 3 is a sectional view illustrating the state where the rigid cover is taken off.
Figure 4:
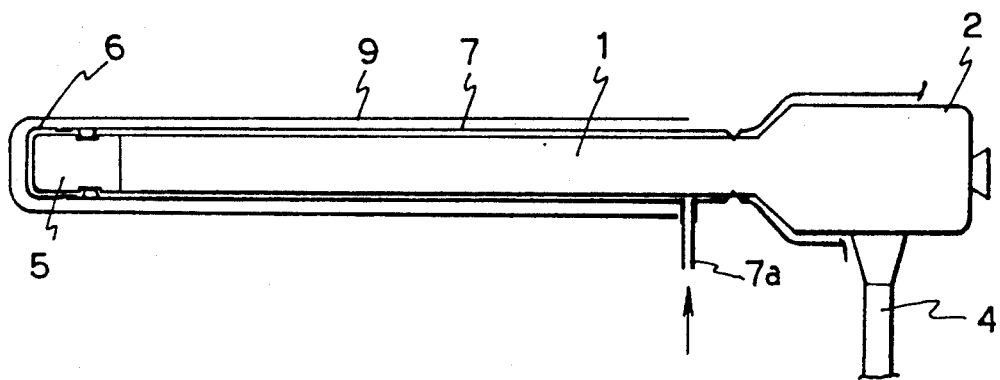
FIG. 4 is a diagram illustrating the state where the endoscope cover is taken off from the endoscope.

FIG. 1 is a side view illustrating the state where an endoscope cover is attached to an endoscope. FIG. 2 is a perspective view illustrating the state of a distal end rigid portion of the endoscope and a rigid cover. FIG. 3 is a sectional view showing the state where the rigid cover is taken off. FIG. 4 is a diagram illustrating the state where the endoscope cover is taken off from the endoscope. In the drawings, reference numeral 1 represents an endoscope comprising a handle 2, an intermediate conduit portion 3 composed of a flexible tube and a guide tube portion 4 connected to a light source.

In general, an image guide, a light guide and an angle-operating wire are disposed in the intermediate conduit portion 3.

The top portion of the intermediate conduit portion 3 forms a bendable angle portion, and a distal end rigid portion 5 is attached to the top end of the angle portion.

An observation port connected to an image guide and an illuminating port connected to a light guide are formed on the distal end of the distal end rigid portion 5.

Notched faces 5a and 5b confronting each other are formed at symmetric positions on the side face of the distal end rigid portion 5, and an anchoring groove 5c is formed on the circumferential face of the distal end rigid portion 5. Reference numeral 5d represents a joint portion to the intermediate conduit portion 3. One of the notched faces 5a and 5b may act as a fitting groove in which a tube having both the ends opened, such as a forceps guide tube continuous from the intermediate conduit portion 3 to the distal end rigid portion 5 or an air/water supply tube, is fitted. In the present example, this fitting groove is used.

Reference numeral 6 represents a rigid cover, which has a cylindrical shape having an inner diameter sufficient to cover the distal end rigid portion 5, and transparent windows 6b and 6c are formed on a closed face 6a on the top end of the rigid cover 6 to confront the observation port and illuminating port and two anchoring projections 6d and 6e are formed at confronting positions on the inner circumferential face of the rigid cover 6. A hood 6f extended to the outer periphery of the top end is formed. If necessary, a hole corresponding to the above-mentioned fitting groove is formed on the closed face 6a and the end portion of the tube 6g having both the ends opened, such as the forceps guide tube, is attached to this hole. Of course, this hole need not be formed in case of an endoscope not using a forceps or the like, and in this case, the above-mentioned fitting groove and the tube having both the ends opened need not be formed.

A soft bag-shaped covering member 7 formed of a rubber or synthetic resin is attached to the outer periphery of the rigid cover 6, and the diameter of the covering member 7 is adjusted to a value almost equal to the outer diameter of the intermediate conduit portion 3 so that the covering member 7 adheres closely to the intermediate conduit portion 3, or adjusted to a value slightly larger than the outer diameter of the intermediate conduit portion 3 so that the covering member 7 loosely covers the intermediate conduit portion 3. In each case, the end portion of the covering member 7 adheres and anchors closely to the intermediate conduit portion 3 at the position of the root of the handle 2 or covers the handle 2 entirely. At the rear portion of the covering member 7, an air-injecting opening 7a is formed so that air can be injected into the covering member 7 from this air-injecting opening 7a.

In the example having the above-mentioned structure, if the rigid cover 6, headed by the covering member 7, is fitted to cover the top end rigid portion 5 of the endoscope, the anchoring projections 6d and 6e are anchored to the anchoring groove 5c of the top end rigid portion 5 by one touch because of the flexibility of the rigid cover 6 and the holes 6b and 6c are positioned and fixed to confront the observation port and illuminating port.

Then, the covering member 7 is extended from the rear part along the intermediate conduit portion 3 and bonded to all or a part of the surface of the intermediate conduit portion 3 to cover the intermediate conduit portion 3 entirely or to cover the handle 2 as well as the intermediate conduit portion 3. In this case, an adhesive can be applied to the handle 2 according to need. In this state, the intermediate conduit portion 3 is inserted into the body cavity and used for the observation.

The adhesive 8 can be applied by brush coating or spray coating, or a double-coated adhesive tape can be used. Furthermore, there can be adopted a method in which the adhesive 8 is not applied to the top end rigid portion 5 or the intermediate conduit portion 3, but the adhesive 8 is applied to the covering member 7 in advance.

After the observation, the endoscope cover is taken out from the endoscope. Namely, at first, the rigid cover 6 is depressed from the outside at positions separate by 90° from the positions of the anchoring projections 6d and 6e (these positions are preferably marked), that is, at the corresponding positions of the notched faces 5a and 5b of the distal end rigid portion 5, as shown in FIG. 3, whereby the rigid cover 6 is elliptically deformed and expanded and the anchoring projections 6d and 6e are taken off from the anchoring groove 5c. In this state, the rigid cover 6 can be removed from the top end rigid portion 5 by pulling. These procedures will now be described in due order.

As shown in FIG. 4, the endoscope is put into a transparent bag 9 having a length sufficient to contain the entire endoscope therein or contain at least the entire intermediate conduit portion 3 therein, so that the operation is carried out in the state where the endoscope is grasped through the bag 9.

At first, air is injected under pressure into the covering member 7 from the air-injecting opening 7a to peel the covering member 7 from the intermediate conduit portion 3 and separate the endoscope cover from the endoscope, and as pointed out hereinbefore, the rigid cover 6 is depressed from the outside at positions separate by 90° from the positions of the anchoring projections 6d and 6e, whereby the anchoring projections 6d and 6e are taken off from the anchoring groove 5c. Therefore, the rigid cover 6 can be taken out from the top end rigid portion 5 and the intermediate conduit portion 3 can be drawn out from the endoscope cover by pulling it together with the bag 9. The endoscope cover is thrown away together with the bag 9, and the endoscope is not contaminated.

Accordingly, by attaching a new endoscope cover to the endoscope, the endoscope can be immediately used again.

In the foregoing example, the notched faces confronting each other are formed by cutting out a part of the circumference flatly in the distal end rigid portion. However, formation of two confronting notched faces is not absolutely necessary, but formation of one notched face in the top end rigid portion suffices if the rigid cover is deformed and the anchoring projections are taken off from the anchoring groove.

As is apparent from the foregoing detailed description, according to the present device, there is provided an endoscope cover comprising a cylindrical rigid cover composed of an elastic material, which is fitted to an endoscope to cover a top end rigid portion of the endoscope, a transparent window arranged on a closed face formed on the distal end of the rigid cover to confront at least an observation port and an illuminating port, which are arranged on the distal end of the endoscope, and a bag-shaped covering member having a length covering at least an intermediate conduit portion of the endoscope, which is attached to the rear part of the endoscope, wherein a groove or notched face is formed in the longitudinal direction of the outer periphery of the distal end rigid portion of the endoscope and an anchoring groove is formed on the circumferential face portion, anchoring projections are formed at confronting positions on the inner circumferential face of the rigid cover and are fitted in the anchoring groove formed in the distal end rigid portion to attach the rigid cover to the distal end rigid portion, and the covering member is bonded to all or a part of the periphery of the intermediate conduit portion by using an adhesive. In this structure, even if the endoscope is used, for example, in the body cavity, since the intermediate conduit portion, that is, the inserting portion, is covered with the covering member, the endoscope is not contaminated, and only by exchanging the endoscope cover with a new endoscope cover after the use, the endoscope can be immediately used again.

Moreover, since the rigid cover is bonded to the distal end rigid portion and the covering member is bonded to the intermediate conduit portion 3, the rigid cover is prevented from being taken off or getting out of position, and there can be attained an effect of ensuring complete covering.

Moreover, since the endoscope cover can be taken off from the endoscope by one touch, the removal of the used endoscope cover can be accomplished without contamination of the endoscope. This is another effect attained by the present device.

What is claimed is:

1. In combination, an endoscope having a distal end with an observation port and an illumination port and a handle, and an endoscope cover comprising a stiff flexible cylindrical end portion adapted to fit over said distal end of said endoscope, said endoscope cover further comprising a covering portion attached to said stiff flexible cylindrical end portion, said covering portion substantially conforming to the shape of said endoscope and extending from the stiff flexible cylindrical end portion to said handle, groove means formed in the distal end of said endoscope, anchoring projections formed in said stiff flexible cylindrical end portion to fit into said groove means to fixedly attach said endoscope cover to said endoscope, thereof separated from a covering portion of said stiff flexible cylindrical end portion, said stiff flexible cylindrical end portion being deformable to move said anchoring projections away from fitting into said groove means, whereby the endoscope cover can be removed by merely pressing on said flexible cylindrical end portion so as to move said anchoring projections out of said groove means.

2. The invention of claim 1, further comprising a transparent bag having a length sufficient to contain the entire endoscope for covering said endoscope and enable visual observation of the removal of said endoscope cover from said endoscope.

3. The invention of claim 1, wherein said distal end of said endoscope comprises at least two notched faces which are spatially separated from said stiff flexible cylindrical end portion permitting depression of said flexible end portion to elliptically deform said stiff flexible cylindrical end portion permitting the endoscope cover to be removed from said endoscope.

4. The invention of claim 3, wherein said two notched faces are located on the opposite sides of the cylindrical portion of said distal end of said endoscope.

5. The invention of claim 4, further comprising a transparent bag having a length sufficient to contain the entire endoscope for covering said endoscope and enable visual observation of the removal of said endoscope cover from said endoscope.

6. The invention of claim 1, wherein the endoscope covering portion is secured to said endoscope.

7. The invention of claim 6, wherein securing means attach said endoscope covering portion to said endoscope.

8. The invention of claim 7, wherein said securing means comprises an adhesive.

9. The invention of claim 7, wherein said securing means are spaced along said endoscope covering portion.

* * * * *